United States Patent
Heil et al.

(10) Patent No.: US 6,743,214 B2
(45) Date of Patent: Jun. 1, 2004

(54) WITHDRAWAL SPIKE

(75) Inventors: Norbert Heil, Felsberg (DE); Bernd Siemon, Melsungen (DE); Klaus Siemon, Koerle (DE)

(73) Assignee: B. Braun Melsungen AG, Melsungen (DE)

( * ) Notice: Subject to any disclaimer, the term of this patent is extended or adjusted under 35 U.S.C. 154(b) by 171 days.

(21) Appl. No.: 09/963,034

(22) Filed: Sep. 26, 2001

(65) Prior Publication Data

US 2002/0040206 A1 Apr. 4, 2002

(30) Foreign Application Priority Data

Sep. 30, 2000 (DE) .......................... 200 16 945

(51) Int. Cl.7 ............................... A61B 19/00
(52) U.S. Cl. ....................... 604/414; 604/411
(58) Field of Search ................. 604/411, 414, 604/905, 43, 93.01, 122, 164.01, 164.06, 164.11, 167.01–167.04, 246–249, 264, 272

(56) References Cited

U.S. PATENT DOCUMENTS

| | | | |
|---|---|---|---|
| 4,128,098 A | | 12/1978 | Bloom et al. |
| 4,588,403 A | * | 5/1986 | Weiss et al. ................. 604/411 |
| 5,254,117 A | * | 10/1993 | Rigby et al. .................. 606/46 |
| 5,269,771 A | | 12/1993 | Thomas et al. |
| 5,385,553 A | * | 1/1995 | Hart et al. ............. 604/167.03 |
| 5,429,256 A | * | 7/1995 | Kestenbaum ............... 215/247 |
| 5,527,306 A | | 6/1996 | Haining |
| 6,224,568 B1 | * | 5/2001 | Morimoto et al. ............ 604/89 |
| 2002/0193777 A1 | * | 12/2002 | Aneas ........................ 604/411 |

FOREIGN PATENT DOCUMENTS

| | | |
|---|---|---|
| DE | 3820204 C2 | 12/1989 |
| DE | 29913550 U | 11/1999 |
| WO | 9619154 A | 6/1996 |
| WO | 9908036 A | 2/1999 |

* cited by examiner

Primary Examiner—Angela D. Sykes
Assistant Examiner—Leslie Deak
(74) Attorney, Agent, or Firm—Diller, Ramik & Wight

(57) ABSTRACT

The withdrawal spike comprises a piercing thorn (10) and a housing (12) having filter chambers for air and fluid. In a connecting piece (23) for connection of an external device a self-closing valve (31) is arranged. Said valve (31) is adapted to prevent fluid from unintentionally flowing out of the withdrawal spike.

6 Claims, 2 Drawing Sheets

WITHDRAWAL SPIKE

BACKGROUND OF THE INVENTION

The present invention relates to a withdrawal spike for withdrawing medical liquids from containers.

A withdrawal spike, as is e. g. described in the patent DE 38 20 204 C2, comprises a piercing thorn having a ventilation duct and a fluid duct. The piercing thorn is connected with a gripping portion on which a connecting piece connected with the fluid duct is arranged. When the withdrawal spike is used, the piercing thorn penetrates through the elastomeric stopper of a bottle or any other container. Then a syringe or a hose line is connected to said connecting piece. The fluid container can be suspended upside down such that, during the withdrawal process, fluid may flow out of and air may enter the container. The withdrawal spike is further suitable for supplying fluid to the container.

The company B. Braun Melsungen AG, Germany, sells a withdrawal spike under the tradename Mini-Spike Plus. The connecting piece of said withdrawal spike is surrounded by a protective jacket which comprises a hinged cover. The closable protective jacket serves, on the one hand, as protection against contamination of the connecting piece, and prevents, on the other hand, uncontrolled leakage of fluid into the surroundings.

When heparin is withdrawn, all heparin syringes of the entire hospital ward are normally drawn up at a time. The piercing thorn is inserted into a heparin bottle and the latter is placed upside down for withdrawal purposes. The syringes placed in readiness, which have been taken out of their sterile packing, are successively connected to the connecting piece of the withdrawal spike and placed into the respective syringe packing after the withdrawal. During exchange of the syringes to be connected to the connecting piece of the withdrawal spike, the person drawing up the syringes continues to hold the bottle in the hand in an upside down manner. If the syringes are not exchanged very rapidly, heparin may drip from the open connecting piece and contaminate the surroundings.

In the case of cytostatic agents, which are toxic, the personnel always fears that the already opened bottles may fall over and become leaky. Therefore such bottles are frequently seal-welded into a PE-bag. The hinged cover of the Mini-Spike Plus spike is generally considered tight and safe.

In some countries it is common practice to use withdrawal spikes in conjunction with bags, i. e. a perfusor syringe is filled with the contents of a bag. This involves the danger of dripping.

SUMMARY OF THE INVENTION

It is an object of the present invention to provide a withdrawal spike offering a maximum of tightness and application reliability and a high degree of cleanliness, hygiene and comfort.

According to the present invention the connecting piece comprises a self-closing valve which is opened by insertion of a tube into the connecting piece. This reliably prevents dripping. In the valve according to the present invention the function of the protective jacket is essentially limited to the prevention of a contact contamination of the connecting piece. Protection against the leakage of fluid is offered by the valve which is in the open position only when a tubular object is pressed into the connecting piece.

Valves, which are opened by insertion of a tubular object, are known in the medical field, mainly for use in conjunction with hose connections, such as catheter connections.

According to the present invention a self-closing valve is integrated in the connecting piece of a withdrawal spike. This causes only a negligible additional expenditure which however offers considerable advantages with regard to application. For example, the exchange of syringes while drawing up heparin syringes is substantially facilitated. In the case of cytostatic agents the danger of the personnel coming in contact with toxic fluids is minimized. Further, the present invention offers advantages with respect to withdrawal of fluids from bags during which process the danger of uncontrolled leakage of fluid is particularly large. The fluid seal does not become effective only at the outlet of the connecting piece but already at its inlet such that the inner wall of the connecting piece is also protected against contamination.

BRIEF DESCRIPTION OF THE DRAWINGS

Hereunder an embodiment of the present invention is described in detail with reference to the drawings in which.

DESCRIPTION OF THE PREFERRED EMBODIMENT

Figure 1:
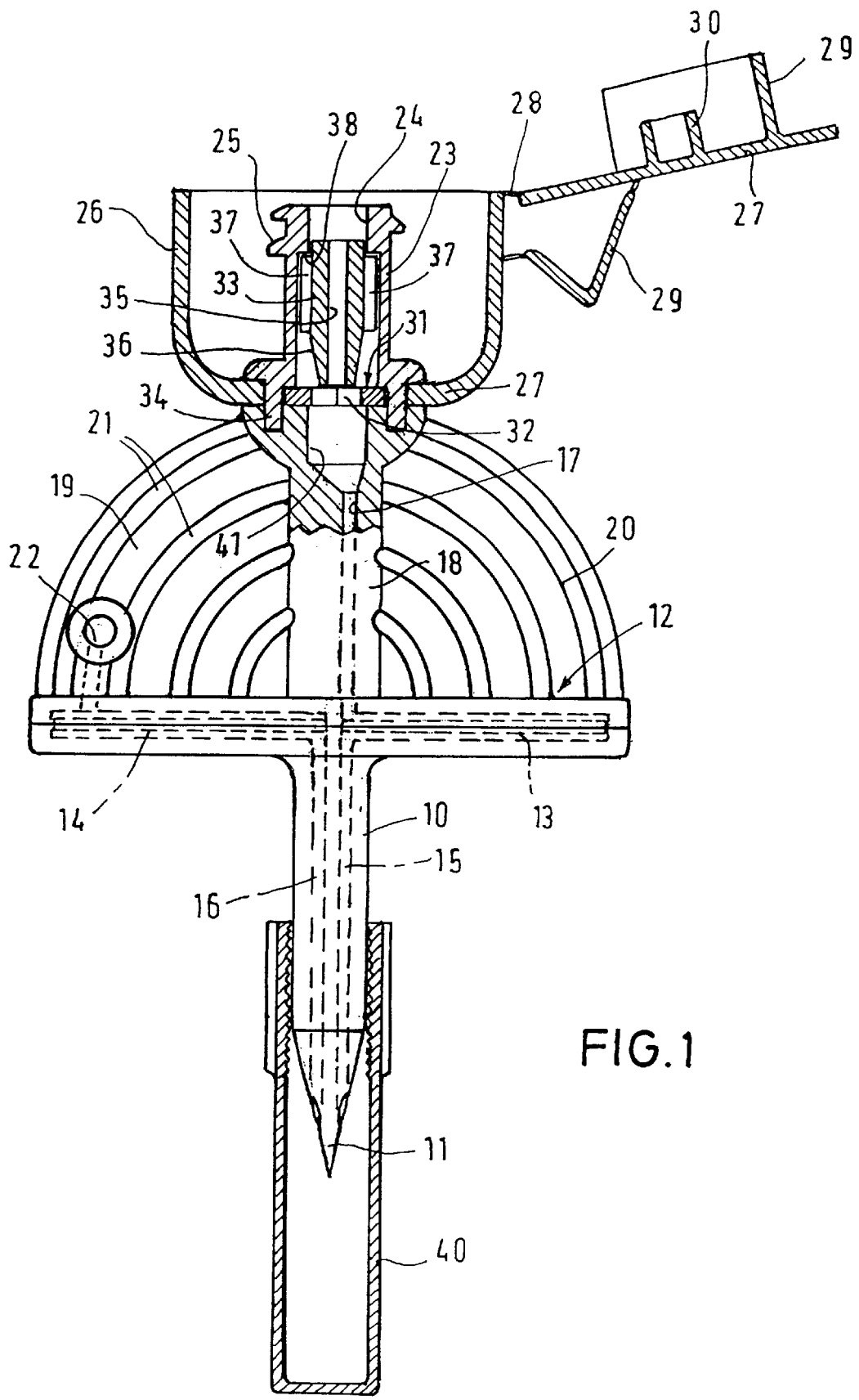
FIG. 1 a part-sectional side view of the withdrawal spike.
Figure 2:
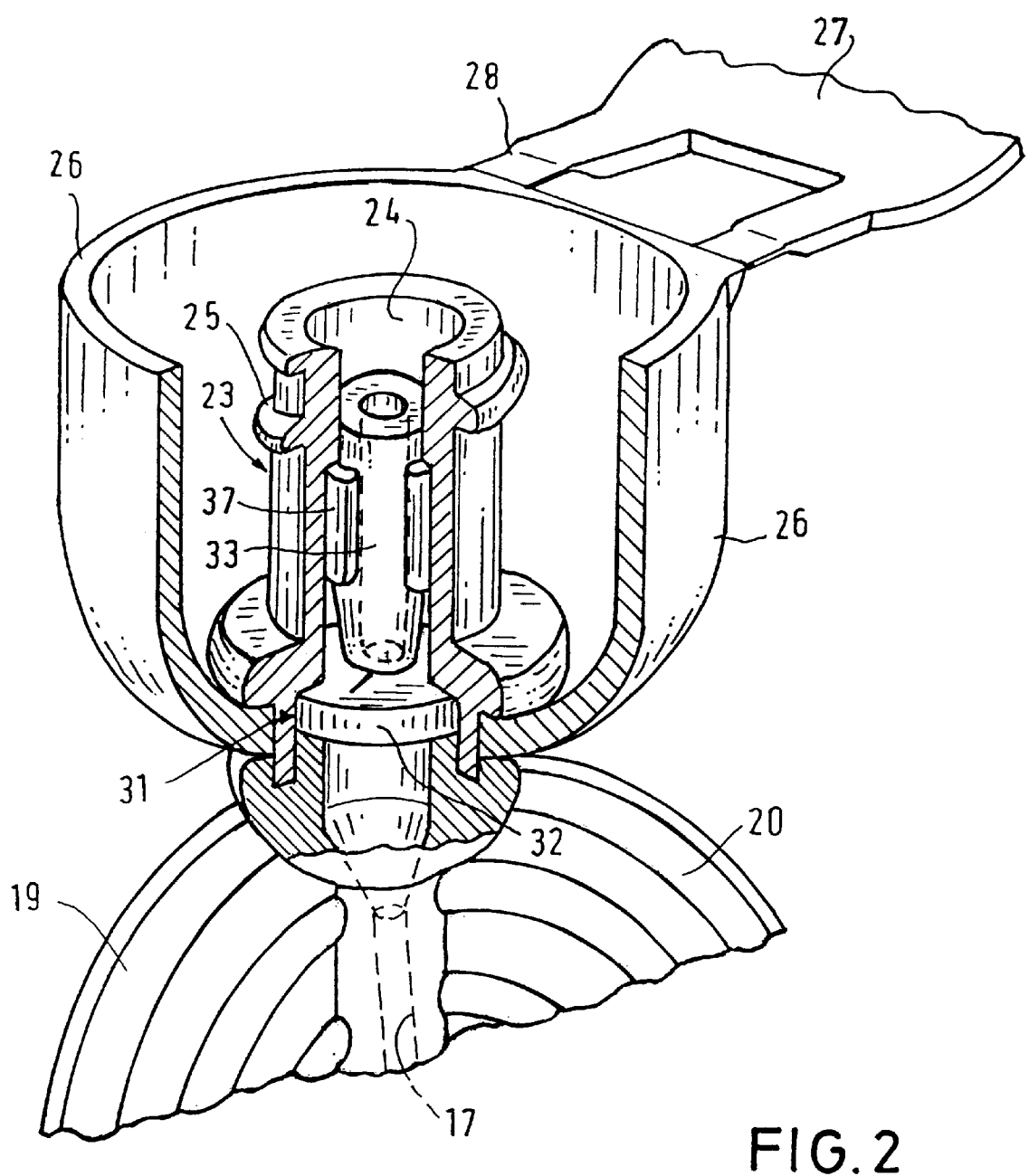
FIG. 2 a part-sectional perspective view of the connecting piece and the surrounding protective jacket.

The shown withdrawal spike comprises a piercing thorn 10 having at its one end a tip 11 for piercing the stopper of a bottle or any other container, and being on its other end integrally formed with a housing 12. Said housing 12 is of plate-shaped configuration and acts as a carrier plate from which the piercing thorn 10 centrally protrudes. The housing 12 comprises a first filter chamber 13 containing a fluid filter and a second filter chamber 14 containing an air filter. Said air filter has a mesh width of 0.45 $\mu$m, and said fluid filter is a particle filter with a mesh width of 5 $\mu$m.

The piercing thorn 10 is provided with a removable protective cap 40.

A fluid duct 15 and an air duct 16 extend in longitudinal direction through the piercing thorn 10. Said two ducts 15, 16 end in the conical area of the tip 11 of the piercing thorn 10. Inside the housing 12 the ducts 15, 16 are isolated from each other. The fluid duct 15 communicates with the filter chamber 13, and the air duct 16 communicates with the filter chamber 14. The filter chamber 13 is further connected with a duct 17 which extends through a tube 18 which, in extension of the piercing thorn 10, is connected with the housing 12 and protrudes to the opposite side of the housing 12. Two wing-shaped portions 19, 20 laterally engage with the tube 18, said wing-shaped portions 19, 20 being configured as quadrantal sectors and extending between the tube 18 and the housing 12. The two wing-shaped portions 19, 20 together form a semicircle located in a plane extending at right angles to the plane of the plate-shaped housing 12. On both sides of the wing-shaped portions 19, 20 concentric ribs 21 are provided which facilitate the gripping by hand. Thus the wing-shaped portions 19, 20 form a gripping part, and the plate-shaped housing 12 forms a manually actuated impact surface when the piercing thorn 10 is inserted into a stopper.

In the wing-shaped portion 19 a vent hole 22 communicating with the filter chamber 14 is provided. In the air flow path the air filter membrane contained in the filter chamber 14 is arranged between the air duct 16 and the vent hole 22.

At the end of the tube 18 a connecting piece 23 having an inner cone 24 and externally threaded ribs 25 of a Luer-Lock connector is arranged. Said connecting piece 23 is annularly surrounded, at a lateral distance, by a protective jacket 26. Said protective jacket 26 comprises a bottom portion 27 sealingly adjoining the base part of the connecting piece 23. The protective jacket 26 protrudes beyond the outer end of the connecting piece 23. At the edge of the pot-shaped protective jacket 26 a hinged cover 27 is fastened by a living hinge 28. Said cover 27 is further connected via a toggle joint arm 29 with the protective jacket 26. Said toggle joint arm 29 effects a snapping behaviour of the cover 27 which assumes either the open position shown in FIG. 1 or the closed position. On the inside of the cover a projecting edge 39 is arranged which, in the closed position of the cover 27, fittingly engages with the protective jacket 26. Further, a cylindrical closing part 30 is provided on the inside of the cover 27, said closing part 30 entering the inner cone 24 of the connecting piece 23.

Inside the connecting piece 23 the valve 31 is arranged. Said valve 31 comprises a valve disk 32 and a valve opener 33. The edge of said valve disk 32 of elastomeric material is clamped between the edge of the tube 18 and an edge of the connecting piece 23 and is gripped over by a sleeve 34 of the connecting piece 23. The valve disk 32 comprises a slot or opening structure. It is of the self-closing type, i. e. without exertion of external pressure it assumes the closed position shown in the drawings.

The valve opener 33 is a tubular part containing a longitudinal duct 35 and a truncated cone 36 at its end, said truncated cone 36 pushing against the central portion of the valve disk 32. On the circumferential area of the valve opener 33 projections 37 protruding to the outside are arranged which are distributed over the circumference. The upper ends of said projections 37 push against an annular shoulder 38 inside the connecting piece 23. Above the annular shoulder 38 the inner cone 24 is located.

Below the valve disk 32 a cavity 41, which is enlarged relative to the duct 17, is provided, and the valve disk 32 can move into said cavity 41 when it is deformed by the valve opener 33.

During use of the withdrawal spike a male Luer cone is placed upon the connecting piece 23, or the cone of a syringe is inserted into the inner cone 24. During this process the penetrating part pushes against the front face of the valve opener 33 whereby the latter is displaced inside the connecting piece 23 thus pressing the valve disk 32 open. The valve 31 is thus forced to remain in the open position as long as the external part protrudes into the connecting piece 23. Thereafter the spring action of the valve disk 32 causes valve opener to return 33 into its initial position, and the valve 31 closes again.

Any fluid residues in the connecting piece 23 or in the valve 31 are prevented from flowing out by closing the cover 27.

Although a preferred embodiment of the invention has been specifically illustrated and described herein, it is to be understood that minor variations may be made without departing from the spirit and scope of the invention, as defined in the appended claims.

What is claimed is:

1. A withdrawal spike for piercing a stopper of a medical container to withdraw medical fluids therefrom comprising
   a piercing thorn (10) having a ventilation duct (16) and a fluid duct (15),
   a gripping part (19, 20) connected with said piercing thorn (10),
   a connecting piece (23) united with the gripping part (19, 20) and having an insertion duct (24),
   a protective jacket (26) surrounding said connecting piece (23) in outward spaced relationship thereto, said protective jacket (26) including a hinged cover (27) which closes a space containing said connecting piece (23),
   a self-closing valve (31) arranged in a fluid path defined at least in part by said fluid duct (15) a tubular valve opener (33) within said connecting piece (23) and being movable to open said valve (31) and, said valve (31) being constructed and arranged for opening by insertion of a tube into said connecting piece (23) which moves said connecting piece (23) to open said valve (31).

2. The withdrawal spike according to claim 1 wherein the valve (31) comprises one of a punched, unpunched or slotted valve disk (32) clamped at an edge thereof.

3. The withdrawal spike according to claim 2 wherein the valve opener (33) is constructed as a truncated cone (36) at an end portion facing the valve disk (32).

4. The withdrawal spike according to claim 1 wherein the valve opener (33) includes outer projections (37) which press against an annular shoulder (38) of the connecting piece (23).

5. The withdrawal spike according to claim 1 wherein the cover (27) includes a closing part (30) which in the closed position closingly engages with the connecting piece (23).

6. The withdrawal spike according to claim 1 wherein the connecting piece (23) is a Luer-Lock connector.

* * * * *